US011742959B2

(12) United States Patent
Phillips et al.

(10) Patent No.: US 11,742,959 B2
(45) Date of Patent: Aug. 29, 2023

(54) SYSTEM AND METHOD FOR WIRELESS COMMUNICATIONS

(71) Applicant: Medtronic, Inc., Minneapolis, MN (US)

(72) Inventors: William C. Phillips, Minneapolis, MI (US); Andrew L. Schmeling, Minneapolis, MI (US)

(73) Assignee: Medtronic, Inc., Minneapolis, MN (US)

( * ) Notice: Subject to any disclaimer, the term of this patent is extended or adjusted under 35 U.S.C. 154(b) by 44 days.

(21) Appl. No.: 17/411,212

(22) Filed: Aug. 25, 2021

(65) Prior Publication Data

US 2023/0069569 A1 Mar. 2, 2023

(51) Int. Cl.
*H04B 15/00* (2006.01)
*A61B 50/33* (2016.01)
*A61N 1/372* (2006.01)

(52) U.S. Cl.
CPC ............. *H04B 15/00* (2013.01); *A61B 50/33* (2016.02); *A61N 1/37217* (2013.01)

(58) Field of Classification Search
CPC ...... H04B 15/00; H04B 15/02; H04B 1/0475; H04B 1/10; H04B 1/1009; A61B 50/30; A61B 50/31; A61B 50/33; A61N 1/37217
See application file for complete search history.

(56) References Cited

U.S. PATENT DOCUMENTS

| | | |
|---|---|---|
| 5,592,939 A | 1/1997 | Martinelli |
| 5,772,594 A | 6/1998 | Barrick |
| 5,913,820 A | 6/1999 | Bladen et al. |
| 5,983,126 A | 11/1999 | Wittkampf |
| 6,940,941 B2 | 9/2005 | Gregerson et al. |
| 7,001,045 B2 | 2/2006 | Gregerson et al. |
| 7,106,825 B2 | 9/2006 | Gregerson et al. |
| 7,108,421 B2 | 9/2006 | Gregerson et al. |
| 7,188,998 B2 | 3/2007 | Gregerson et al. |
| 7,751,865 B2 | 7/2010 | Jascob et al. |
| 8,287,816 B2 * | 10/2012 | Kral ...................... B62B 5/0026 422/1 |
| 8,457,755 B2 | 6/2013 | Snitting |
| 8,842,893 B2 | 9/2014 | Teichman et al. |
| 9,403,596 B2 * | 8/2016 | Pajic ....................... H02J 7/342 |
| 9,737,235 B2 | 8/2017 | Hartmann |
| 9,769,912 B2 | 9/2017 | Helm et al. |
| 11,394,835 B1 * | 7/2022 | Bindana ................. H04N 1/126 |
| 2004/0199072 A1 | 10/2004 | Sprouse et al. |
| 2007/0205121 A1 * | 9/2007 | Pearce .................. H04B 1/3888 206/320 |

* cited by examiner

*Primary Examiner* — Quochien B Vuong
(74) *Attorney, Agent, or Firm* — Harness, Dickey & Pierce, P.L.C.

(57) ABSTRACT

Disclosed is a system for reducing or eliminating interference during communication. Disclosed is a system to position an implantable medical device at an orientation or position to reduce or eliminate interference. Therefore, a communication may be maintained with the IMD over a selected period of time.

15 Claims, 9 Drawing Sheets

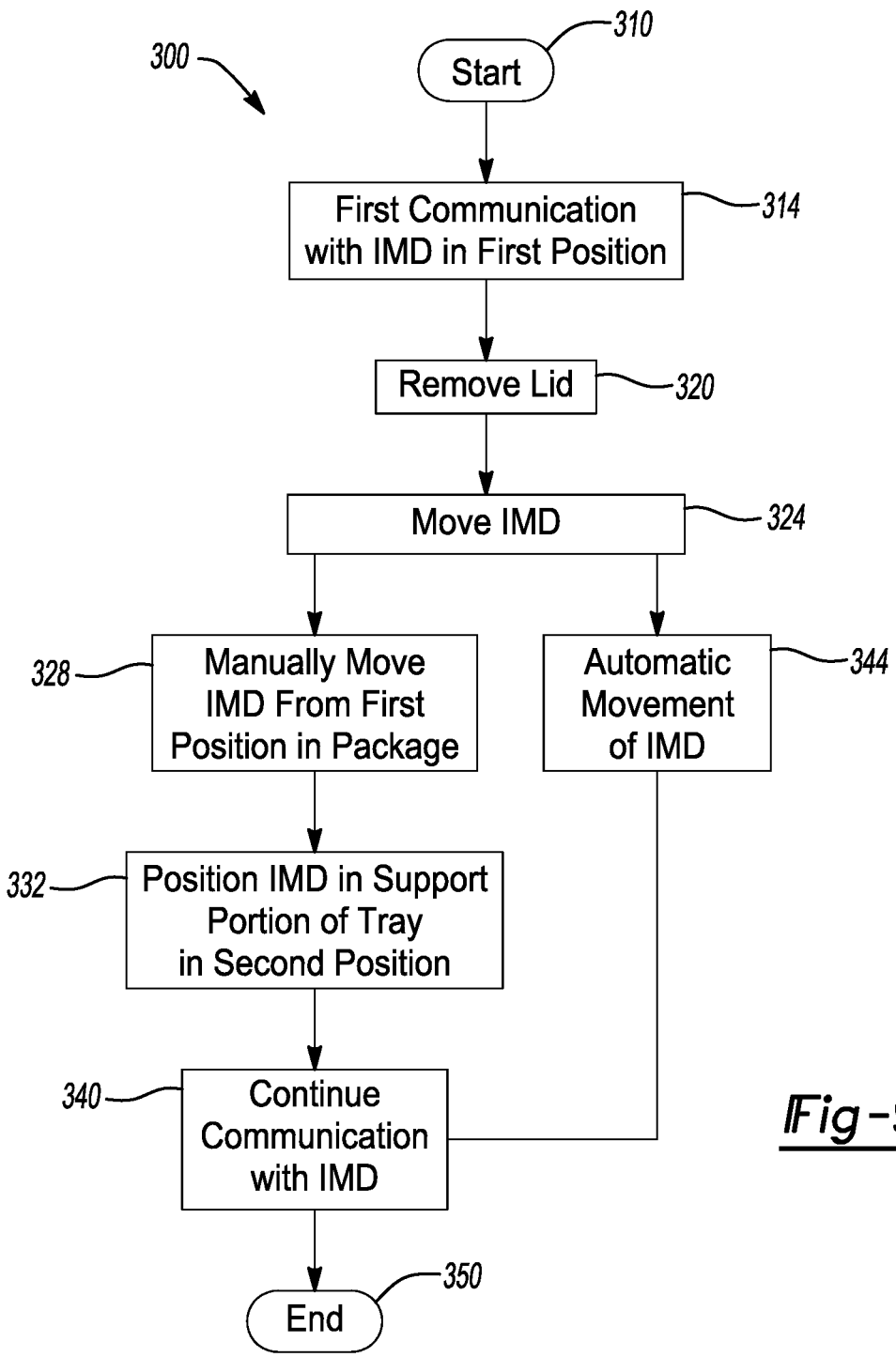

SYSTEM AND METHOD FOR WIRELESS COMMUNICATIONS

FIELD

Disclosed is a system for reducing or eliminating interference during receiving and transmitting data, and particularly to a system that reduces the interference.

BACKGROUND

This section provides background information related to the present disclosure which is not necessarily prior art.

A device may be provided to provide therapy to a subject. The device may be programmed to provide a selected therapy over a selected period of time to the subject. For example, an implantable cardiac device (ICD) or an implantable neurostimulator (INS) may be implanted in the subject. The subject may include a human subject or any other appropriate subject. The device may be programmed to provide therapy to the subject over a period of time, such as stimulation to various portions of the subject. For example, the ICD may stimulate a cardiac portion of the subject to provide appropriate rhythm for the subject. The INS may be used to stimulate various neurons or neuropathways of a subject for various purposes, such as pain and relief.

SUMMARY

This section provides a general summary of the disclosure, and is not a comprehensive disclosure of its full scope or all of its features.

Disclosed is a system provided to reduce or eliminate interference for communication with a device. For example, an implantable device may include an antenna that receives and/or transmits a signal. The signal, for example, may be a wireless signal provided to or from a programmer. The programmer may include a device that is operated by a user to provide instructions and/or receive data from the implantable device.

The system may include a container to position the implantable device such that it is spaced away from an interfering object. An interfering object may include a conductive surface or object near the implantable device. For example, the implantable device may be positioned near a metallic table during or prior to an implantation procedure. The container may hold the implantable device away or spaced apart from the metallic table to reduce and/or eliminate interference with the transmissions to or from the implantable device.

The container includes a portion to hold the implantable device at a selected orientation or position away from the outer surface of the container. Accordingly the implantable device may communicate with a programmer regardless of the environment adjacent to a portion of the container position and assists in reducing possible interference from an interfering object that is in contact with the surface of the container. The container may include a portion to receive the implantable device by movement from a user. The container may further include mechanisms to move the implantable device after or upon releasing a retaining member or force on the implantable device, such that movement of the implantable device is substantially automatic.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 9 is a flowchart of a process.

Corresponding reference numerals indicate corresponding parts throughout the several views of the drawings.

DETAILED DESCRIPTION

Example embodiments will now be described more fully with reference to the accompanying drawings.

Figure 1:
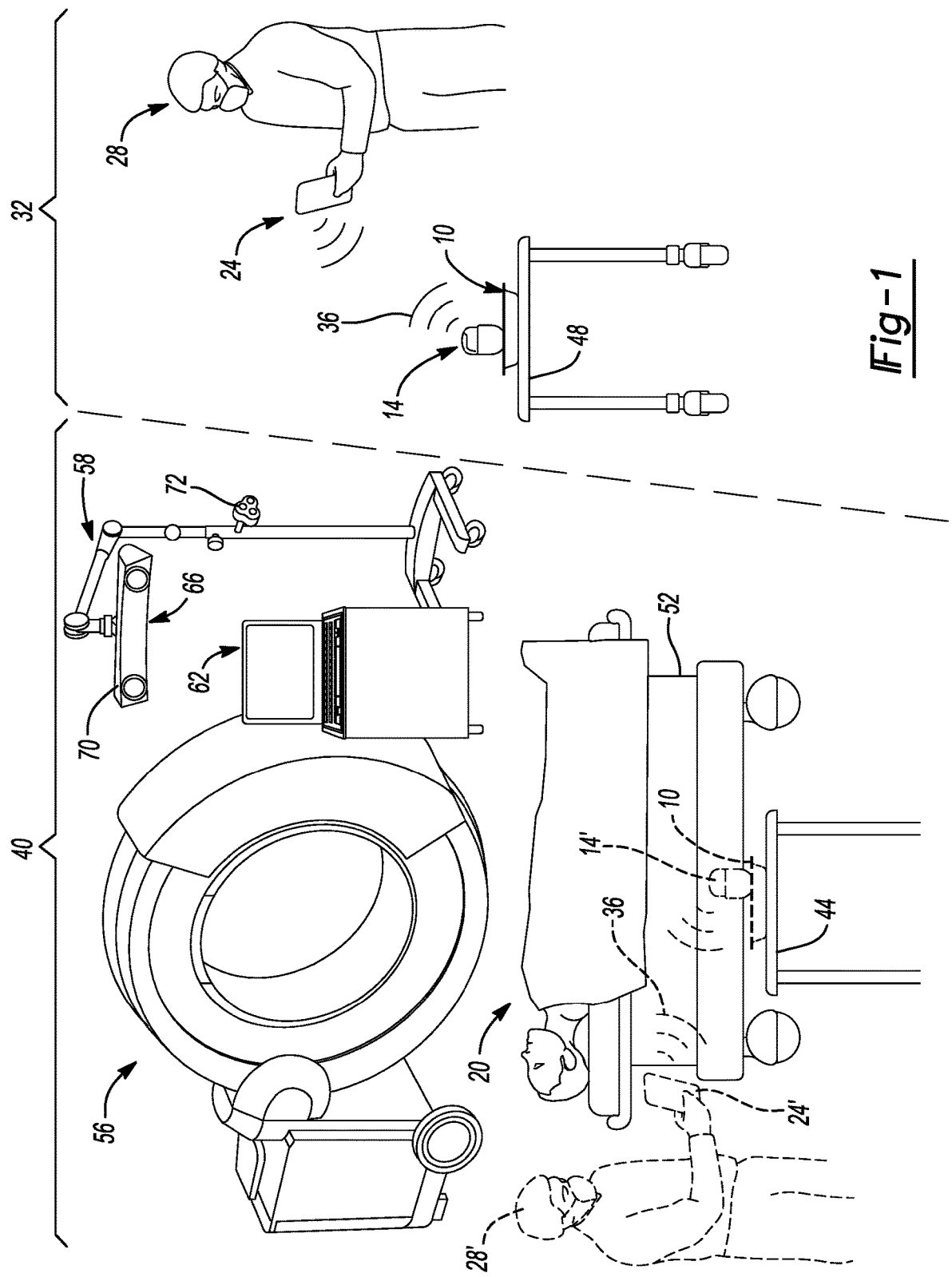
FIG. 1 is a schematic environmental view of a system to reduce interference during a wireless transmission.

FIG. 1 illustrates a system which may include a container assembly or system 10. The container assembly 10 may be used to contain and/or orient a device, such as an implantable medical device (IMD) 14. The IMD 14 may be provided for various purposes, such as providing therapy to a subject 20. The IMD 14 may be programmed with a programmer 24 that may be operated by a user 28 to program the IMD 14 to provide therapy to the subject 20. The subject 20 may be any appropriate subject, such as a living or non-living subject. Further, the subject 20 may include a human subject. In various embodiments, however, the device 14 may be a device that is positioned in a non-living subject, such as an airframe or automobile that may be programmed, as discussed further herein, at a first instance or location and positioned for operation at a second instance or location.

In various embodiments, the user 28 may initiate communication with the IMD 14 from the programmer 24 at first instance or location 32. In the first instance, for example, the user 28 may be in a first area or position such as in the non-sterile area 32. The non-sterile area 32 may be in a first room, a first section of a room, such as a preparation table 48, or other area or location. The IMD 14 may communicate with the programmer 24 in a wireless manner, such as via a wireless signal 36. The wireless signal 36 may be a transmission with any appropriate protocol, including those discussed further herein.

The device 14 may then be moved in a second area or further programmed in a second area 40, such as in the second or optional location. The device 14', illustrated in phantom, may have constant communication with the programmer 24 during movement to and within the second location 40. The user 28, illustrated as the phantom 28' may interact with the programmer 24' to wirelessly communicate with the IMD 14'. The IMD 14' in the container 10' may be positioned on a table or platform 44 that may be formed of a conductive material, or other material, which may interfere with the wireless communication between the programmer 24' and the device 14'. In the first instance, such as in the non-sterile area 32, the IMD 14 may be positioned on the non-interfering table or platform 48 for an initial communication or syncing between the programmer 24 and the IMD 14. In various embodiments, the first table 48 may also be interfering and positioning the IMD 14 in a selected orientation, as discussed herein, may allow for communication with the programmer 28.

In various embodiments, the sterile or second area 40 may include an operating theater where the subject 20 is prepared for implantation of the IMD 14. Accordingly, the subject 20 may be placed on a platform, such as an operating room table 52. The sterile area 40 may include an operating theater that may further include an imaging device 56. The imaging device 56 may be the O-Arm® imaging device, sold by Medtronic, Inc. The imaging device 56 may further include the imaging device as disclosed in U.S. Pat. Nos. 9,769,912; 7,188,998; 7,108,421; 7,106,825; 7,001,045; and 6,940,941 all incorporated herein by reference. The operating theater 40 may further include a navigation system 58 that includes a user interface or operating terminal 62, which may include a processor, memory, user input, display device, and the like. Further, the navigation system 58 may include one or more localizer assemblies 66 such as an optical localizer 70 and/or an electromagnetic localizer 72. The navigation system may include navigation systems such as those disclosed in U.S. Pat. Nos. 5,772,594; 5,913,820; 5,592,939; 5,983,126; 7,751,865; and 8,842,893; and 9,737,235 and those disclosed in U.S. Pat. App. Pub. No. 2004/0199072, all incorporated herein by reference. Accordingly, the operating theater 40 may include or be a sterile area that is separate from the first area 32, that may be non-sterile, and may include various interfering objects such as the table or platform 44. The interfering device or portions 44 may interfere with a wireless communication between the programmer 24 and the IMD 14. It is understood by one skilled in the art that the first area 32 the second area 40 may be separated by a distance such that they are separate locations.

The IMD 14 in the container 10, is illustrated in FIG. 1 and further illustrated in FIGS. 2 and 3 and will be described in greater detail. The IMD 14 may be any appropriate IMD, such as one or more of the Intellis™ implantable neurostimulator sold by Medtronic, Inc. The IMD 14, therefore, may have one or more portions that are enclosed within a housing 80. The housing 80 may be formed of a selected material, such as a metal or other appropriate material. Extending from the housing 80 may be a connector and/or antenna portion 84. The antenna portion 84 may have an antenna to allow for communication wirelessly with the programmer 24. Included within the IMD 14 may also be a processor 88 and a memory portion 92. The processor 88 may provide instructions to transmit and/or receive signals from the programmer 24 via the antenna 84. Therefore, the IMD 14 may communicate with the programmer 24 including transmitting data to the programmer 24 and/or receiving instructions from the programmer 24. Included within the container 10 may also be an additional instrumentation, such as a probe 96. The probe 96 may be used to activate the IMD 14 such as by a manual manipulation of a portion of the IMD 14.

The IMD 14 may be provided within the container 10, as discussed above and as illustrated in FIG. 2 and FIG. 3. The container 10 may include a lower portion or body portion 100 that may include various depressions, such as a first depression 104 to receive the probe and a second depression 108 to receive the IMD in a first orientation as illustrated in FIG. 2. The body portion 100 may also be referred to as a tray. The tray 100 may be formed of a material that is generally non-conductive, such as a polymer or with specific high or low conductive properties to provide shielding or isolation. Further, the tray 100, in various embodiments, may be generally or substantially rigid. The tray 100 may be rigid enough to allow a user to press the IMD 14 into a selected region or depression, as discussed herein, without crushing or inelastically deforming. Further, the tracy 100 may provide a support for a biasing member, as also discussed herein. In various embodiments, however, the tray 100 may be pliable depending on the application to hold the medical device 14 in a desired orientation. The tray 100 may be rigid enough to hold the IMD 14 in a first orientation as illustrated in FIG. 2 and in a second orientation as illustrated in FIG. 4. As discussed further, herein, the tray 100 may be rigid enough to provide support for a support or positioning member.

Figure 2:
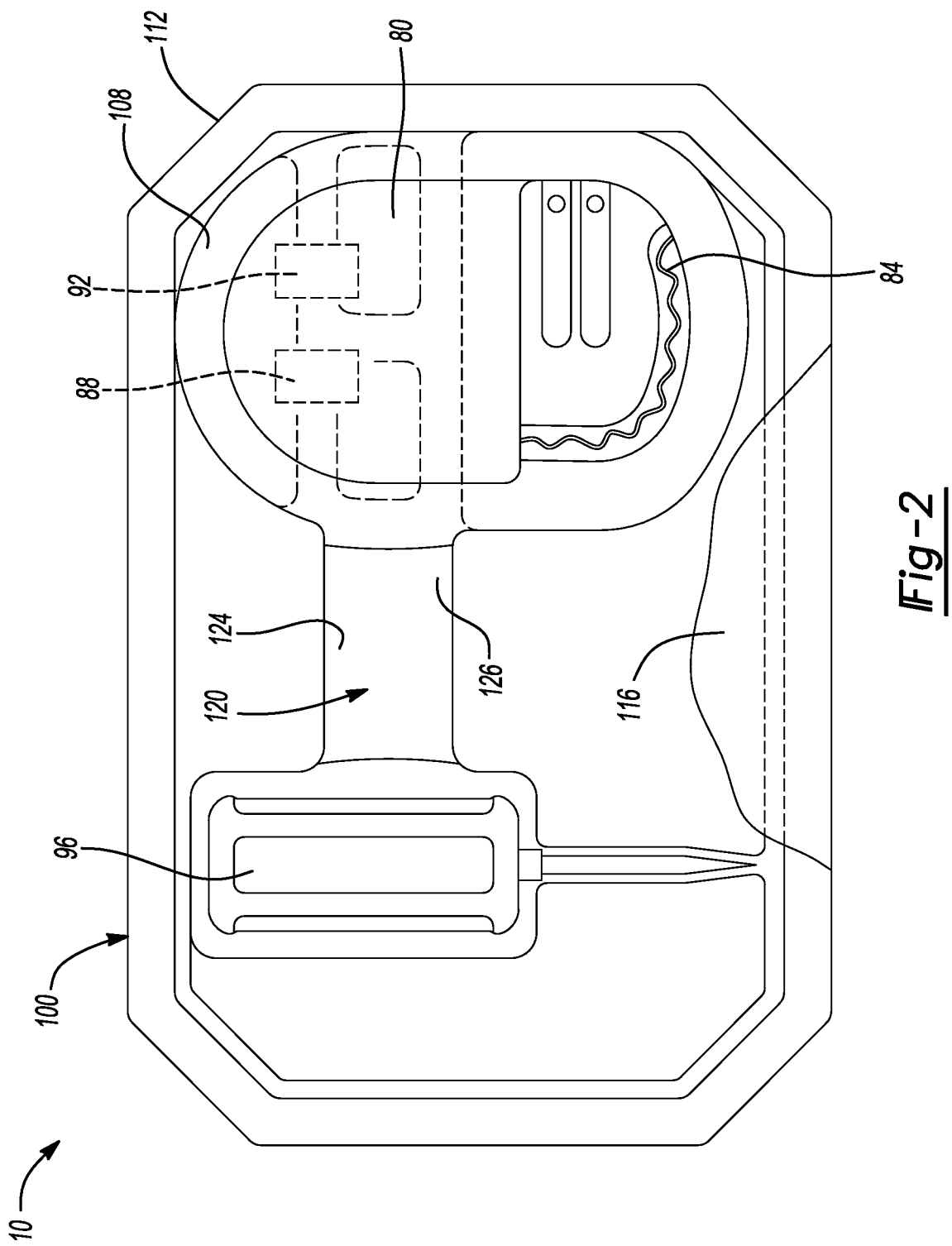
FIG. 2 is a top plan view of a container assembly including an implantable medical device.
Figure 3:
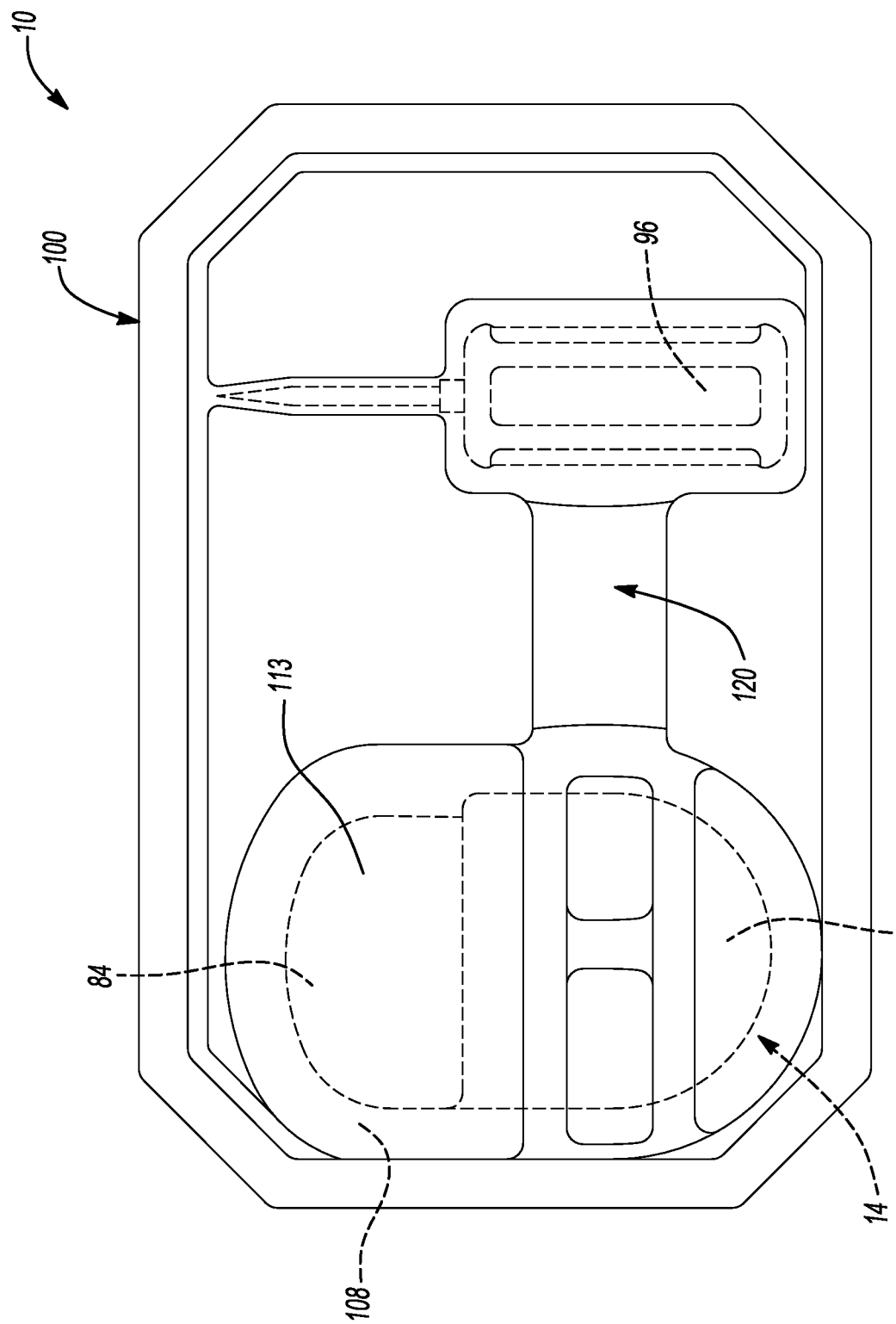
FIG. 3 is a bottom plan view of a container assembly including an implantable medical device.
Figure 4:
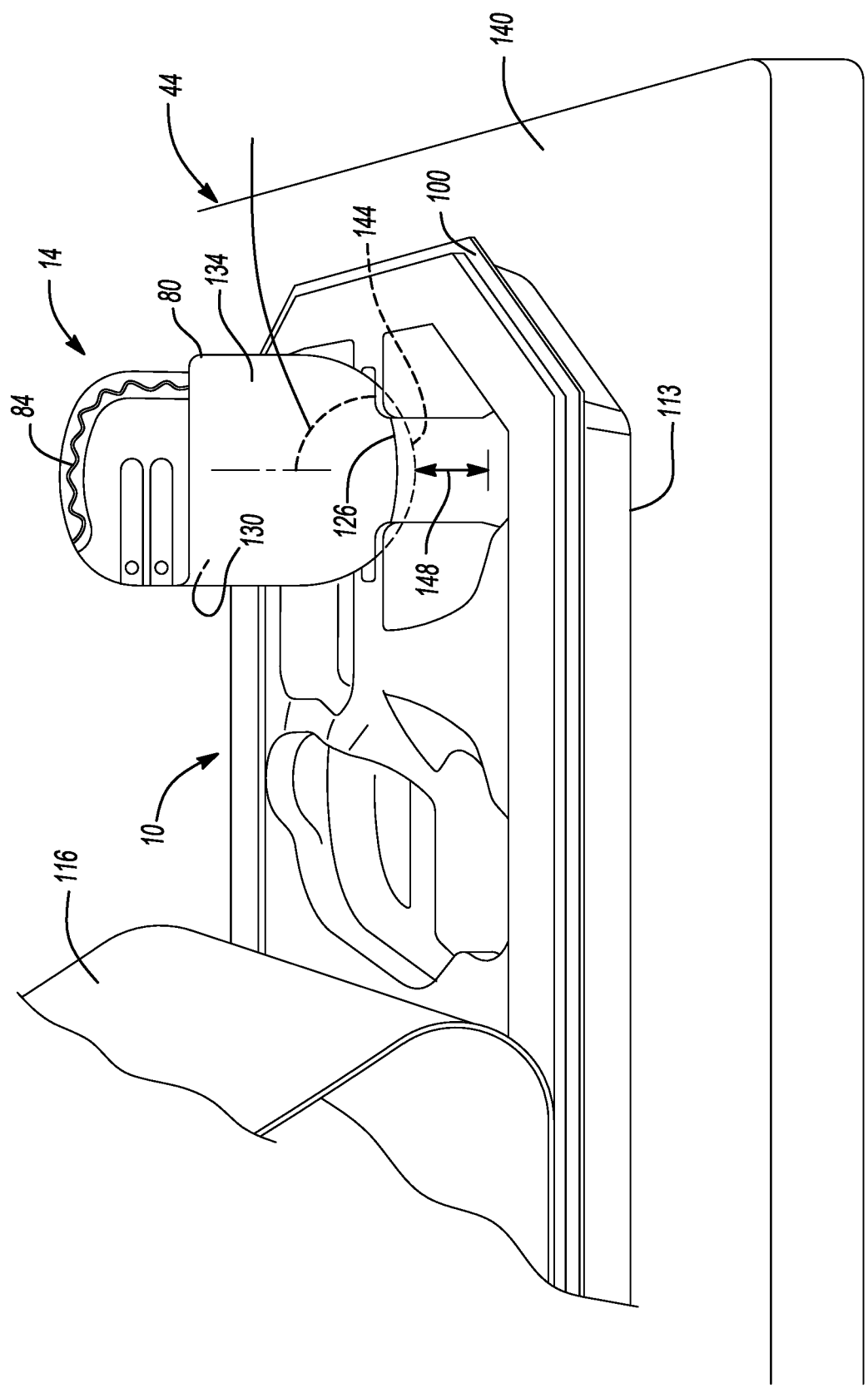
FIG. 4 is a top perspective view of a container assembly holding the implantable medical device in a selected orientation, according to various embodiments.

The IMD 14 as illustrated in FIG. 2 is positioned substantially parallel with a surface, such as an upper surface 112 of the container 100 and/or a bottom or contact surface 113 (FIG. 3). It is understood that the IMD 14 may have a surface that is substantially parallel with the surface 112. The upper surface 112 may have a covering 116. The cover 116 may cover the entirety of the container 100, such as after manufacturing and for delivery of the assembly container 10 for use, such as to the user 28. Accordingly, the cover 116 may be removed at a selected time, such as prior to implantation and for programming of the IMD 14. The cover 116 may be adhered to the edge 112 of the container body 100 such that the cover 116 may be removed by pulling off by the user 28. It is understood that any other appropriate removal of the cover 116 may be performed and that pulling back and tearing is merely exemplary.

Further, the container body 100 may include a positioning well or depression 120. The positioning well 120 may include various features or portions to hold or position the IMD 14 in a selected configuration such as illustrated in FIG. 4. The second configuration as illustrated in FIG. 4 may be an upright configuration such that a portion of the IMD would extend above the contacting or adhesive wall 112. Further, the IMD 14 may be generally or substantially perpendicular to the bottom surface 113. In various embodiments, however, the IMD 14 may be at an angle 123 in the second orientation. The angle 123 may be about 45 degrees to about 130 degrees, including about 80 degrees to about 110 degrees, including about 90 degrees.

Generally the positioning well 120 may include a support surface, such as a first wall 124 and a second wall 126, as illustrated in FIG. 2. The two walls may engage a portion of the case 80 of the IMD 14. For example, the first wall 124 may engage or contact a rear surface 130 of the case 80. The second wall 126 may engage a front surface 134 of the case 80.

As illustrated in FIG. 4, therefore, once the cover 116 is removed from a selected portion, such as a portion including the support well 120, the IMD 14 may be removed from the container shell 100 and oriented in the support well 120. As illustrated in FIG. 4, the container assembly 10 including the container shell 100 may be positioned on the surface 44. The orientation of the IMD 14, however, when positioned in the support well 120, allows for positioning of the antenna portion 84 a distance from the support surface 44, such as an upper surface 140 thereof. In various embodiments, for example, the support well 120 may have a bottom surface 144 that is a distance 148 from the surface 140 of the table 44. The distance 148 may be about 0.5 millimeters (mm) to about 5 mm from the surface 140. The distance 148 may assist in positioning the IMD 14 a selected distance apart from the interfering object 44. The dimensions of the IMD 14 may also position the antenna portion 84 a spaced apart distance from the object 44.

The positioning of the IMD 14, including the case 80 and the antenna portion 84, in the supporting well 120, therefore, positions the antenna portion 84 such that interfering portions are invisible to a communication via the antenna assembly 84. For example, the positioning well 120 may allow for the antenna 84 to be positioned about 0.1 millimeters (mm) to about 100 centimeters (cm), including about 5 mm to about 30 mm from an outer surface of the tray 100 and/or a surface of the interference object. As illustrated in FIG. 1, the programmer 24' may be positioned to communicate with the IMD 14 as the IMD 14 is positioned in the container shell 100 in the support well 120. The communication between the programmer 24 and the IMD 14 may proceed, therefore, regardless of the positioning of the IMD 14 relative to the support surface 44. The tray 100 and the support well 120, therefore, allows the IMD 14 to be positioned relative to selected surfaces while maintaining communication with the programmer 24 regardless of the position of the IMD 14 relative to the surface when the IMD 14 is within the support well 120. The container shell 100 may be used to hold the IMD 14 during a selected procedure where the IMD 14 is positioned adjacent or near interfering objects when the IMD 14 is held within the container support well 120.

In various embodiments, for example, the user 28 may initiate communication with the IMD 14 in the first area or space 32. Thereafter, the user 28 or other appropriate individual may move the IMD 14 while maintaining connection between the IMD 14 and the programmer 24. The support well 120 allows the IMD 14 to be invisible to interfering objects regarding communicating with the program 24.

The IMD 14 may be manually moved from the first position, as illustrated in FIGS. 2 and 3, to the second position as illustrated in FIG. 4. For example, the user 28 may remove the cover 116 and grasp the IMD 14 and physically move it from the first or packaged or flat orientation to a second upright communicating orientation, as illustrated in FIG. 4. This allows the user 28 or any appropriate user to move the IMD 14 between the at least two positions and position the IMD 14 within the supporting well 120.

Turning reference to FIGS. 5, 6, 7, and 8 the IMD 14 may be positioned or oriented between two selected positions substantially automatically. With initial reference to FIG. 5, the IMD 14 may be positioned within a container 200. The container assembly 200 may include a container shell 210 that is covered with a cover 214 that is sealed to a shell sealing portion or region 218, similar to that as discussed above. The container shell 210 may also be referred to as a tray. As discussed above, the tray 210 may be generally rigid. The IMD 14 may be positioned within a well or depression 222 that has a side wall 226 and a bottom wall 228. The IMD 14 may be held within the well 222 by the force resistance of the lid 214 sealed to the shell 210 of the container 200. The IMD 14 is held within the tray 210 by the cover 214

The container assembly 200 may further include a support member or assembly 240. The support assembly 240 may include a first member 244 that may extend from a first side or end 246 to a second side or end 248. The support member 244 may include a selected material that may be elastically deformed or resiliently positioned between the IMD 14 and the bottom wall 228 of the well 222.

The support member 244 by be supported by the tray 210 including the rigid structure and formation of the tray 210. The support member 244 may be formed of a selected material such as a natural or synthetic rubber, a silicone material, a deformable polymer strap, or other appropriate material. The support member 244 is positioned between the IMD 14 and the bottom wall 228 of the container shell 210.

Figure 5:
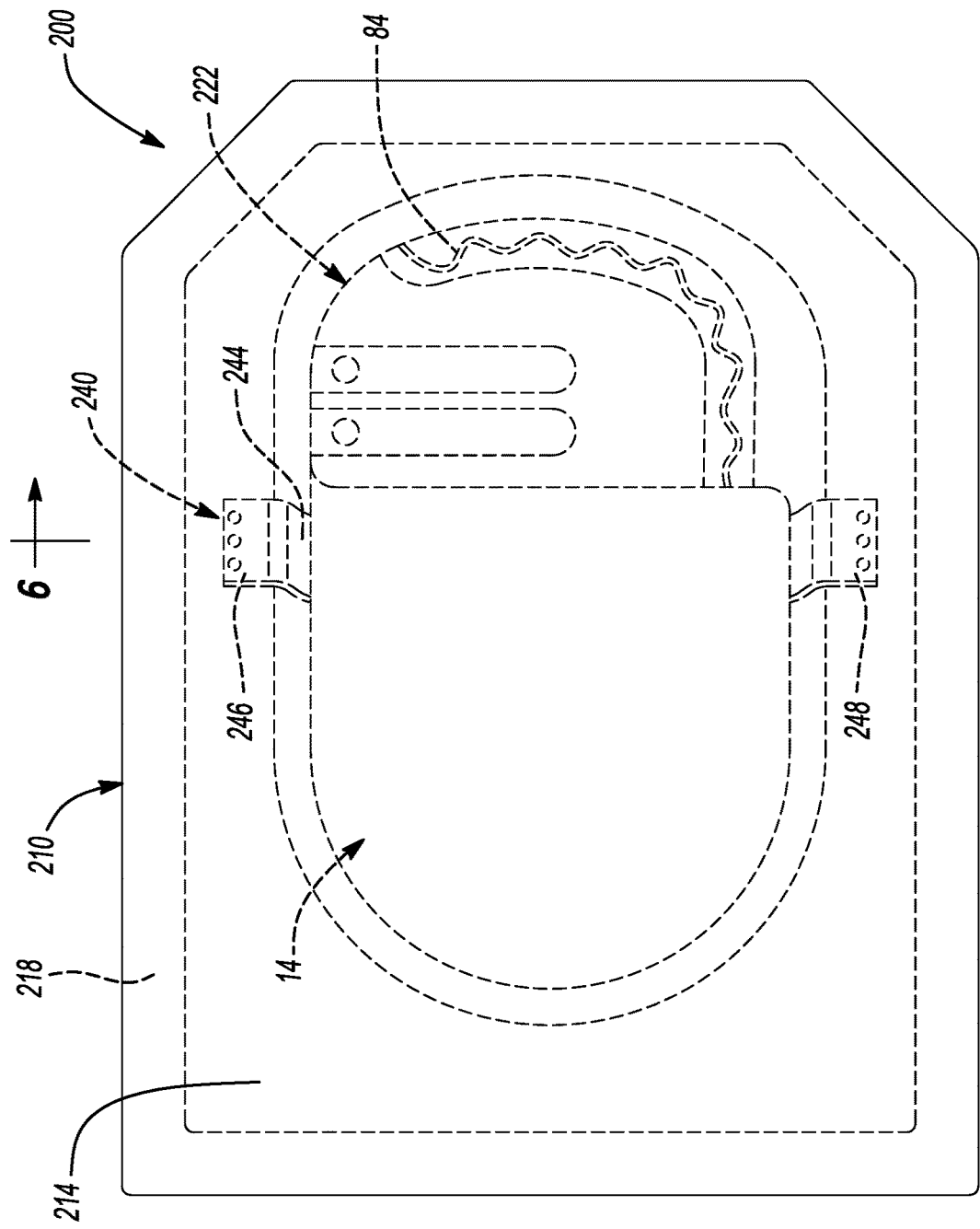
FIG. 5 is a top plan view of a container assembly, containing an implantable medical device, according to various embodiments.
Figure 6:
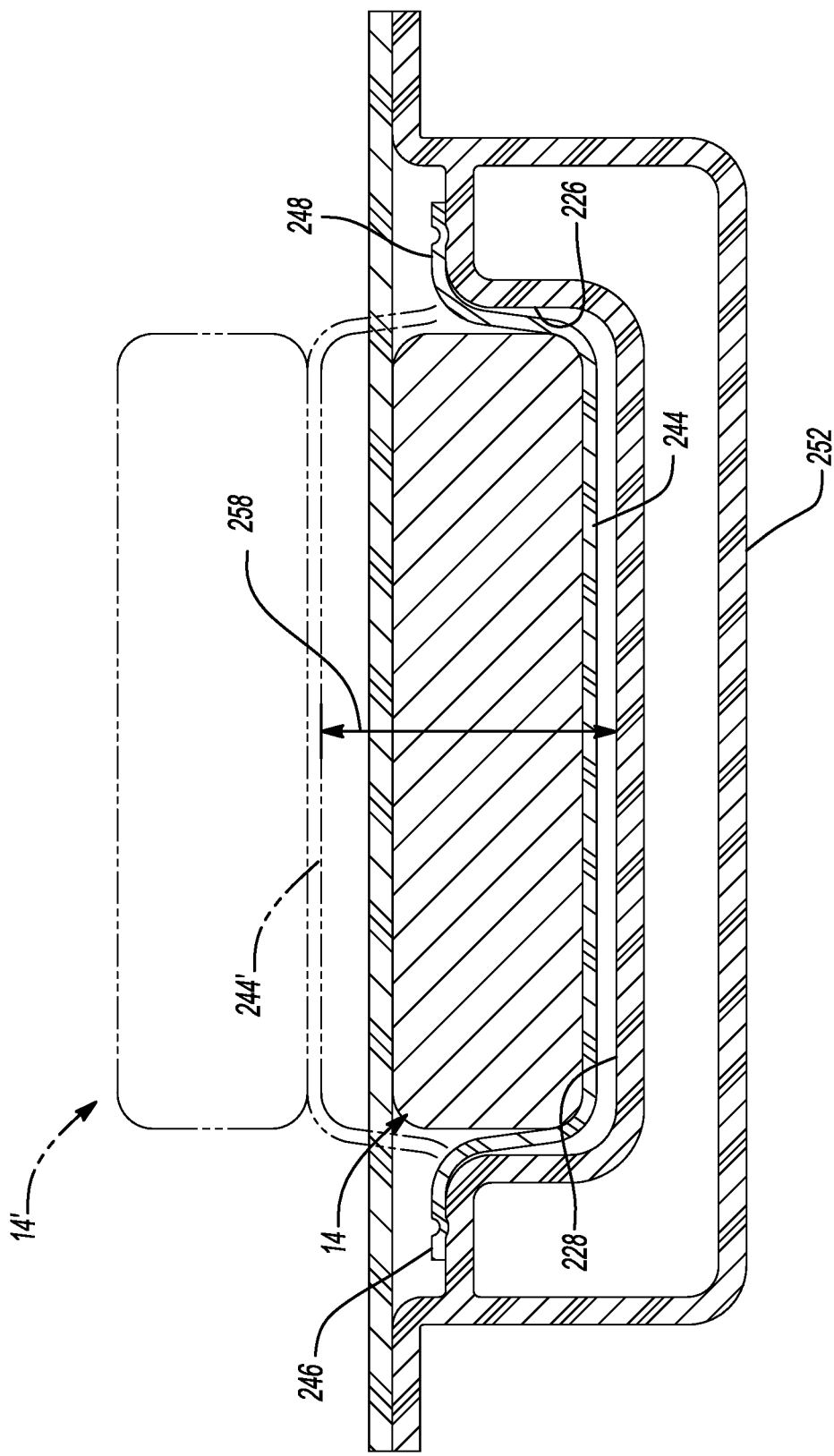
FIG. 6 is cross-section view of the container of FIG. 5 taken along line 6-6 with a device in two orientations.

In a first or stored configuration, as illustrated in FIGS. 5 and 6, the IMD 14 is positioned within the well 222. The IMD 14 may depress or push the support member 244 toward the bottom wall 228 when the lid 214 is positioned over the IMD 14 and sealed to the shell 210. As discussed above, the tray 210 may support the support member 244 when elastically deformed by the IMD 14. Further, the retaining force provided by the lid 214 against and/or onto the IMD 14 resists a movement or resilience of the support member 244 to move the IMD 14 away from a bottom outer surface 252 of the shell or tray 210.

Figure 7:
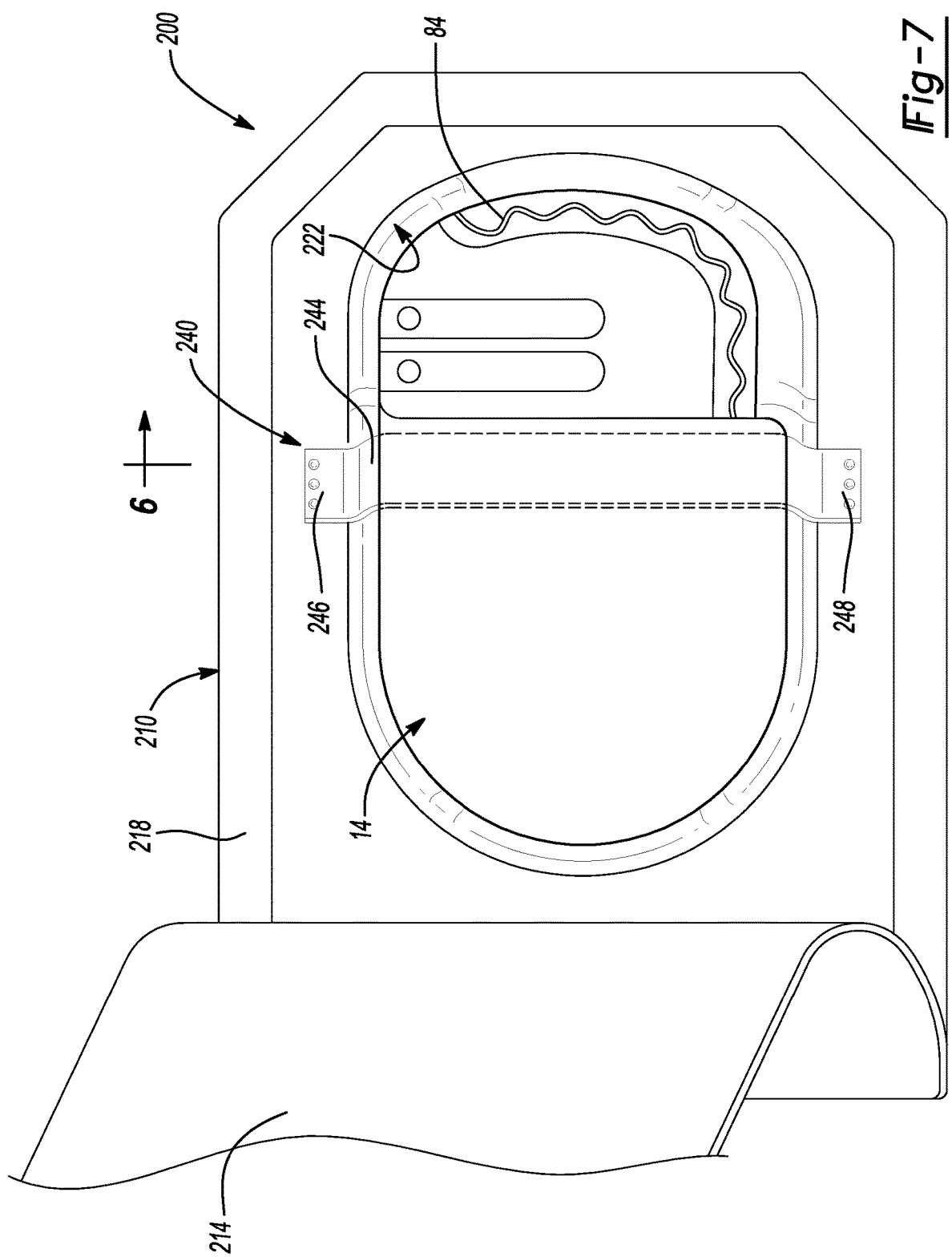
FIG. 7 is a top plan view of a container assembly with a device in a second orientation, according to various embodiments
Figure 8:
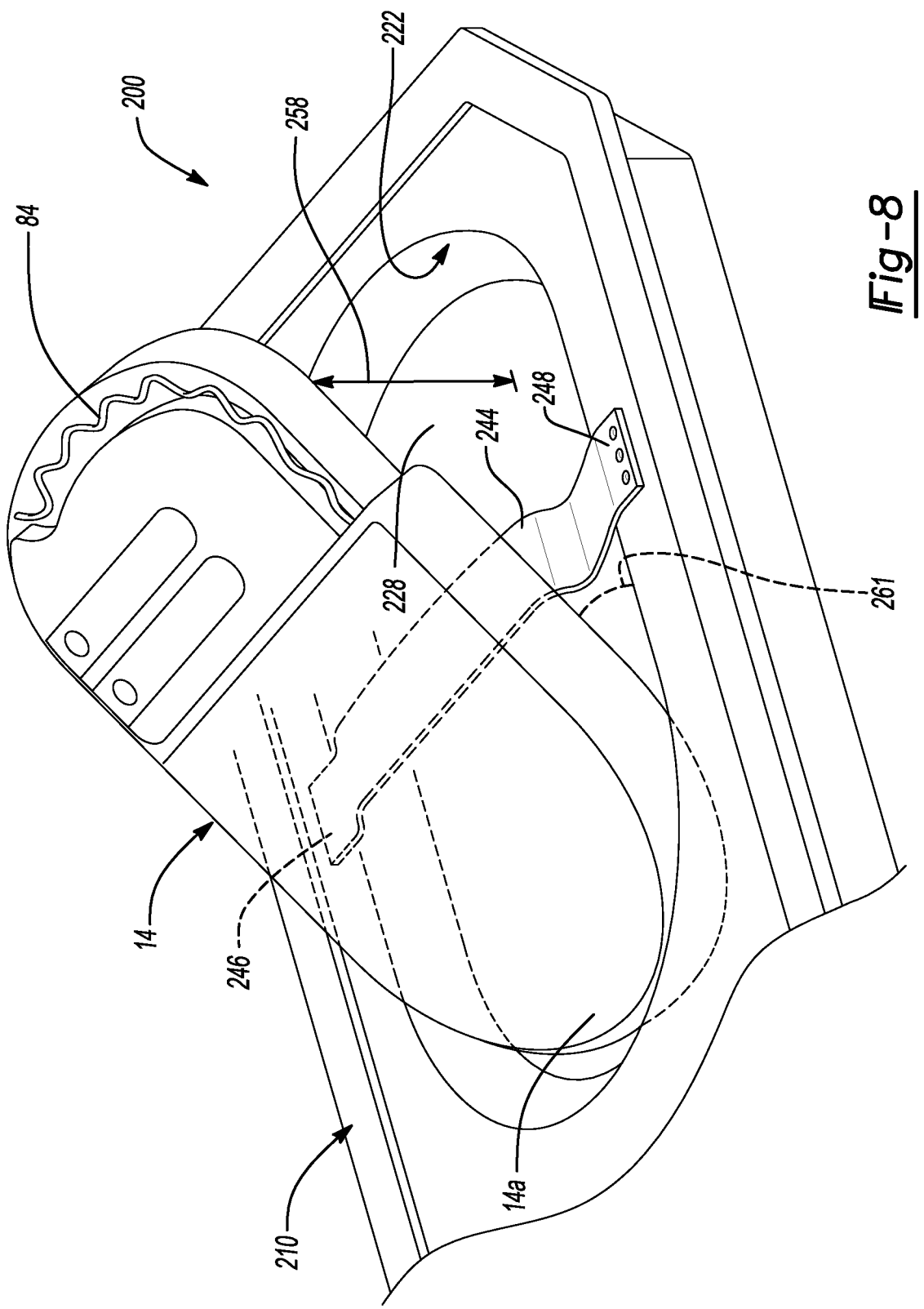
FIG. 8 is top perspective view of the container assembly of FIG. 7 with the device in the second orientation, according to various embodiments.

Upon removal of the lid 214, is illustrated in FIGS. 7 and 8, the support member 244 may resiliently and automatically move away from the bottom surface 228 of the tray 210 and move the IMD 14 therewith without any other user interaction. As illustrated in FIGS. 6-8, for example, the support member 244 may spring or return to a position, such as in up or away position 244', so that the IMD 14 is moved away from the bottom surface 228 of the tray 210. In various embodiments, for example, the IMD 14 may be moved a selected distance 258 away from the bottom surface 228 of the tray 210. The distance 258 may be any appropriate distance such as about 0.1 mm to about 100 cm, including about 0.1 mm to about 100 mm, and further including about 0.1 mm to about 30 mm. As noted above, the IMD 14 may include an antenna region 84 that may be moved at least the distance 258 away from the bottom surface of the well 228.

Accordingly, the IMD 14 may be moved from a position near the bottom wall or surface 228 (i.e., a first position or orientation) to a position away from the bottom wall or surface (i.e., a second position or orientation), such as by the distance 258 due to removal of the lid 214. Thus, the antenna 84 may be a selected distance, such as about 1 mm to about 60 mm, including about 1 mm to about 50 mm from an outer surface of the tray and/or the interfering object. The user 28, therefore, need not engage or contact the IMD 14 to move the IMD 14 to the second position. The well 222 may provide a base or contact surface such that the IMD 14 is held at an angle 261 where a bottom or end 14a, formed a distance from the antenna region 84, is held within the well 222 of the tray 210 while the antenna region 84 is held the distance 258 away from the bottom surface 228 by the support member 244. Again, the support member 244 may be held under tension by the IMD 14 and the lid 214 in the closed position. When the lid 214 is removed the force applied to the IMD 14 and the support member 244 may be removed. When the force of the lid 214 is removed the support member 244 may move away from the bottom surface 228 and, therefore, move the IMD 14. The tray 210, as discussed above, may include a rigidity sufficient to support the support member 244 to move the IMD 14.

As discussed above, the IMD 14 may be positioned in a respective container or container assembly 10, 200 for transport to a selected position. As discussed above, the first position may be in a non-sterile area 32 and the second location may be in a sterile portion 40. Moreover, the user 28 may initiate communication with the IMD 14 in the first position, such as the non-sterile area 32, and continue communication in the sterile area or second area 40. Continuing communication, for example, may include initiating and maintaining a communication connection with a programmer 24 and the IMD 14 when the IMD 14 is moved and in both locations. Therefore, once communication is initiated the communication may be maintained without requiring a re-initiation (e.g., handshake) between the programmer 24 and the IMD 14. The maintenance of the communication may assist in performing or allowing for the performing of a faster procedure or completing a procedure by not requiring a second initiation of communication between the programmer 24 and the IMD 14.

Accordingly, with reference to FIG. 9, a process of communicating and providing the IMD 14 is illustrated in the flowchart 300. The process 300 may initiate or begin in start block 310. Thereafter, a first communication with the IMD may be made in block 314. The first communication may be a startup or initiation of communication steps between the programmer 24 and the IMD 14. In various embodiments, for example, a system check, communication initiation, or the like may be performed by the user 28 at the first position 32. The communication between the programmer 24 and the IMD 14 may be initiated at a first position, such as when an IMD 14 is within the packaging 10, 200 and/or prior to moving the IMD 14 into the second or sterile position 40.

In various embodiments, a lid to the container assembly may be removed in block 320. The lid 320 may be removed before or after initiation of the first communication in block 314. Nevertheless, the removal of the lid of the packaging system 10, 200 may allow access to the IMD 14. After removing the lid in block 320, moving the IMD 14 may occur in block 324. Moving the IMD 14 in block 324 may include moving the IMD 14 to a second position or orientation, as discussed and illustrated above, such as from within a first well or position to a second upstanding position.

In various embodiments, the IMD 14 may be manually moved by the user 28 from a first position in block 328. For example, the user 28 may lift the IMD 14 from the well or holding well 108 within the tray 100. The user 28 may move the IMD 14 to a second or support position in block 332. Again, as discussed above, the IMD 14 may be moved to the support well or area 120 in the tray 100. Thus, the user 28 may move the IMD 14 manually from the first position to the second position such that the IMD 14 is positioned with the antenna 84 at a selected distance or position away from an outer surface of the tray 100. Thereafter, the user 28 may continue communication with the IMD in block 340. Again continuing communication with the IMD in block 340 may include maintaining communication from the programmer 24 when in the first position or area 32 and to the second area 40. The continued communication may be due to the positioning or placement of the antenna a selected distance form an interfering object within the selected tray, as discussed above.

Alternatively or additionally, after removing the lid in block 320 the IMD may be moved in block 324 with an automatic movement of the IMD in 344. Automatic movement of the IMD may include resilient movement repositioning by the support member 244, as discussed above. Accordingly, the user 28 may remove the lid 214 and the support strip 244 may move the IMD 14, as discussed above. The movement of the IMD 14 may, therefore, be substantially automatic or based upon the mechanical portions of the container assembly 200, such as the support strap 244.

Again, after moving the IMD in block 344 continuation of the communication may occur in block 340. With or after the continuation of the communication, the process 300 may end in block 350. It is understood, however, that the process 300 ending in block 350 may be only ending of the maintaining of the communication with the IMD 14 regardless of an interfering object. The user 28 may continue to implant the IMD 14 into the subject 20, perform additional preparation steps, perform further programming or communication with the IMD 14, or the like.

As discussed above, the IMD 14 may be moved from a first position to a second position with the tray 100, 200, as discussed above and/or according to various embodiments. Therefore, the IMD 14 may be maintained in communication with the programmer 24 as it is invisible to various interfering objects, such as the table 44. The IMD 14 may not be in a position to have interference from an object due to the positioning of the IMD 14 in the respective trays 100, 210. Therefore, the communication may continue for various purposes such as programming or maintaining communication with the programmer 24 for a selected period of time.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a special purpose computer created by configuring a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor or module or 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A system to at least reduce an interference of a communication, comprising:
    a packaging assembly having at least a first portion and a second portion;
    wherein the first portion is configured to removably cover the second portion;
    wherein the second portion includes a tray member;
    wherein the tray member includes an inner surface having at least one orienting portion;
    wherein the orienting portion is configured to engage an outer wall of a device to orient the device in a first orientation substantially parallel to an outer surface of the tray member;
    wherein the tray member includes a holding well;
    wherein the holding well is shaped and sized to hold the device in a second orientation substantially upright from the outer surface.

2. The system of claim 1, wherein the first orientation positions a first portion of the device a first distance from the outer surface of the tray member;
    wherein the second orientation positions the first portion of the device a second distance from the outer surface of the tray member;
    wherein the second distance is greater than the first distance.

3. The system of claim 1, wherein the tray member is formed of a rigid non-conducting material.

4. A system to at least reduce an interference of a communication, comprising:
    a packaging assembly having at least a tray member and a lid member, wherein the lid member is configured to removably cover the tray member;
    at least one orienting member connected to an inner surface of the tray member;
    wherein the orienting member has a first connection region and a second connection region;
    wherein the first connection region is fixed to a first tray connection of the tray member and the second connection region is fixed to a second tray connection of the tray member;
    wherein a device is positioned between the first tray connection of the tray member and the second tray connection of the tray member;
    wherein the orienting member is configured to engage an outer wall of the device to orient the device in a first orientation
    wherein in the first orientation the device is held atop the orienting member and between the lid member and the orienting member.

5. The system of claim 4, wherein the orienting member is a biasing member.

6. The system of claim 5, wherein the orienting member is an elastically deformable and resilient member.

7. The system of claim 4, wherein the tray member defines a depression having at least a bottom wall and an end wall;
    wherein the orienting member extends over the depression;
    wherein the device is configured to be held within the depression in the first orientation atop the orienting member.

8. The system of claim 7, wherein the lid member engages the device in a closed configuration to hold the device within the depression atop the orienting member.

9. The system of claim 8, wherein the orienting member holds the device in a second orientation when the lid member is in an open configuration;
    wherein the second orientation, a portion of the device is spaced away from the depression.

10. A method of maintaining communication connection between a first system and a second system at least by reducing interference at the second system, the method comprising:
    providing a packaging assembly having at least a tray member and a lid member;
    providing the lid member to removably cover the tray member;
    providing a first orienting portion of the tray member and a second orienting portion of the tray member;
    providing the first orienting portion of the tray member to hold a device in a first orientation inside the tray member, where the first orientation is substantially parallel to an outer surface of the tray member; and
    providing the second orienting portion of the tray member to hold the device in a second orientation inside the tray member, where the second orientation is substantially upright from the outer surface.

11. The method of claim 10, further comprising:
initiating communication with the device with a programmer in a first location; and
maintaining communication between the device and the programmer when the device is moved to a second location.

12. The method of claim 11, further comprising:
communicating with the device when in the second orientation.

13. The method of claim 12, wherein providing the second orienting portion of the tray member to hold the device in a second orientation includes maintaining the device in an orientation generally vertical relative to the outer surface of the tray member.

14. The method of claim 10, further comprising:
positioning the device in the second orientation portion from the first orientation portion.

15. The method of claim 10, further comprising:
providing at least one orienting member connected to an inner surface of the tray member;
providing the orienting member connected at a first connection region and at a second connection region;
providing the orienting member to move the device to the second orientation within the second orienting portion when the lid member is at least partially removed from the tray member.

\* \* \* \* \*

UNITED STATES PATENT AND TRADEMARK OFFICE
CERTIFICATE OF CORRECTION

| | | |
|---|---|---|
| PATENT NO. | : 11,742,959 B2 | Page 1 of 1 |
| APPLICATION NO. | : 17/411212 | |
| DATED | : August 29, 2023 | |
| INVENTOR(S) | : William C. Phillips et al. | |

It is certified that error appears in the above-identified patent and that said Letters Patent is hereby corrected as shown below:

On the Title Page

Column 1, (72) Inventors, Line 1, Delete "MI" and insert --MN-- therefor

Column 1, (72) Inventors, Line 3, Delete "MI" and insert --MN-- therefor

In the Specification

Column 3, Detailed Description, Line 16, Delete "28." and insert --24.-- therefor Column 4, Detailed Description, Line 18, Delete "tracy" and insert --tray-- therefor Column 4, Detailed Description, Line 35, Delete "assembly container" and insert --container assembly-- therefor Column 5, Detailed Description, Line 45, Delete "program" and insert --programmer-- therefor In the Claims Column 10, Line 29, In Claim 4, after "orientation", insert --;--

Signed and Sealed this
Nineteenth Day of March, 2024

*Katherine Kelly Vidal*
Katherine Kelly Vidal
*Director of the United States Patent and Trademark Office*